(12) United States Patent
Satake et al.

(10) Patent No.: US 7,854,739 B2
(45) Date of Patent: Dec. 21, 2010

(54) CLIP APPARATUS FOR LIGATURING LIVING TISSUE

(75) Inventors: Motoi Satake, Chofu (JP); Koh Kimura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 40 days.

(21) Appl. No.: 11/881,059

(22) Filed: Jul. 25, 2007

(65) Prior Publication Data
US 2008/0027467 A1    Jan. 31, 2008

(30) Foreign Application Priority Data
Jul. 25, 2006   (JP) ............... 2006-202342

(51) Int. Cl.
*A61B 17/08*   (2006.01)
*A61B 17/10*   (2006.01)

(52) U.S. Cl. .................. 606/151; 606/157; 606/142

(58) Field of Classification Search ................. 606/139, 606/142–143, 151, 157–158, 219
See application file for complete search history.

(56) References Cited

U.S. PATENT DOCUMENTS

2002/0045909 A1    4/2002  Kimura et al.
2002/0128667 A1    9/2002  Kobayashi et al.
2005/0143767 A1*   6/2005  Kimura et al. .............. 606/158

FOREIGN PATENT DOCUMENTS

| EP | 1 523 946 A1 | 4/2005 |
| JP | 2002-191609 | 7/2002 |
| JP | 2004-121485 | 4/2004 |

* cited by examiner

*Primary Examiner*—Anhtuan T Nguyen
*Assistant Examiner*—Ashley Cronin
(74) *Attorney, Agent, or Firm*—Scully, Scott, Murphy & Presser, P.C.

(57) ABSTRACT

A clip apparatus for ligaturing a living tissue includes a clip unit provided removably at a distal end of an insertion part inserted into a forceps channel of an endoscope, and an operating part for the unit, extending in an passage of the insertion part. The unit has a clip holder in an opening of the passage and a passage for elastically opening/closing of a clip, an engaging portion to be opened elastically around the passage when the holder projects from the passage, and longitudinally engaged with the distal end of the insertion part, and a structure preventing excessive opening of the engaging portion when a member connected to the clip and the operating part and moving in the passage is broken at a breakable portion by a pulling force from the operating part.

4 Claims, 6 Drawing Sheets

CLIP APPARATUS FOR LIGATURING LIVING TISSUE

CROSS-REFERENCE TO RELATED APPLICATIONS

This application is based upon and claims the benefit of priority from prior Japanese Patent Application No. 2006-202342, filed Jul. 25, 2006, the entire contents of which are incorporated herein by reference.

BACKGROUND OF THE INVENTION

1. Field of the Invention

This invention relates to a clip apparatus for ligaturing a living tissue.

2. Description of the Related Art

Each of Jpn. Pat. Appln. KOKAI Publication Nos. 2002-191609 and 2004-121485 discloses a clip apparatus for ligaturing a living tissue comprising: an insertion part which is to be inserted into a forceps channel of an endoscope inserted into a body cavity of a living thing; a clip unit which includes a clip provided removably at a distal end portion of the insertion part and configured to be opened and closed; and a clip operating part which includes an external operation portion exposed at a proximal end portion of the insertion part and a clip connecting portion extending from the external operation portion to the distal end portion in the insertion part and connected to the clip unit, and which is configured to open and close the clip of the clip unit by operating the external operating portion.

Such conventional clip apparatus for ligaturing a living tissue will be explained hereinafter with reference to FIG. 5 to FIG. 8B.

Figure 5:
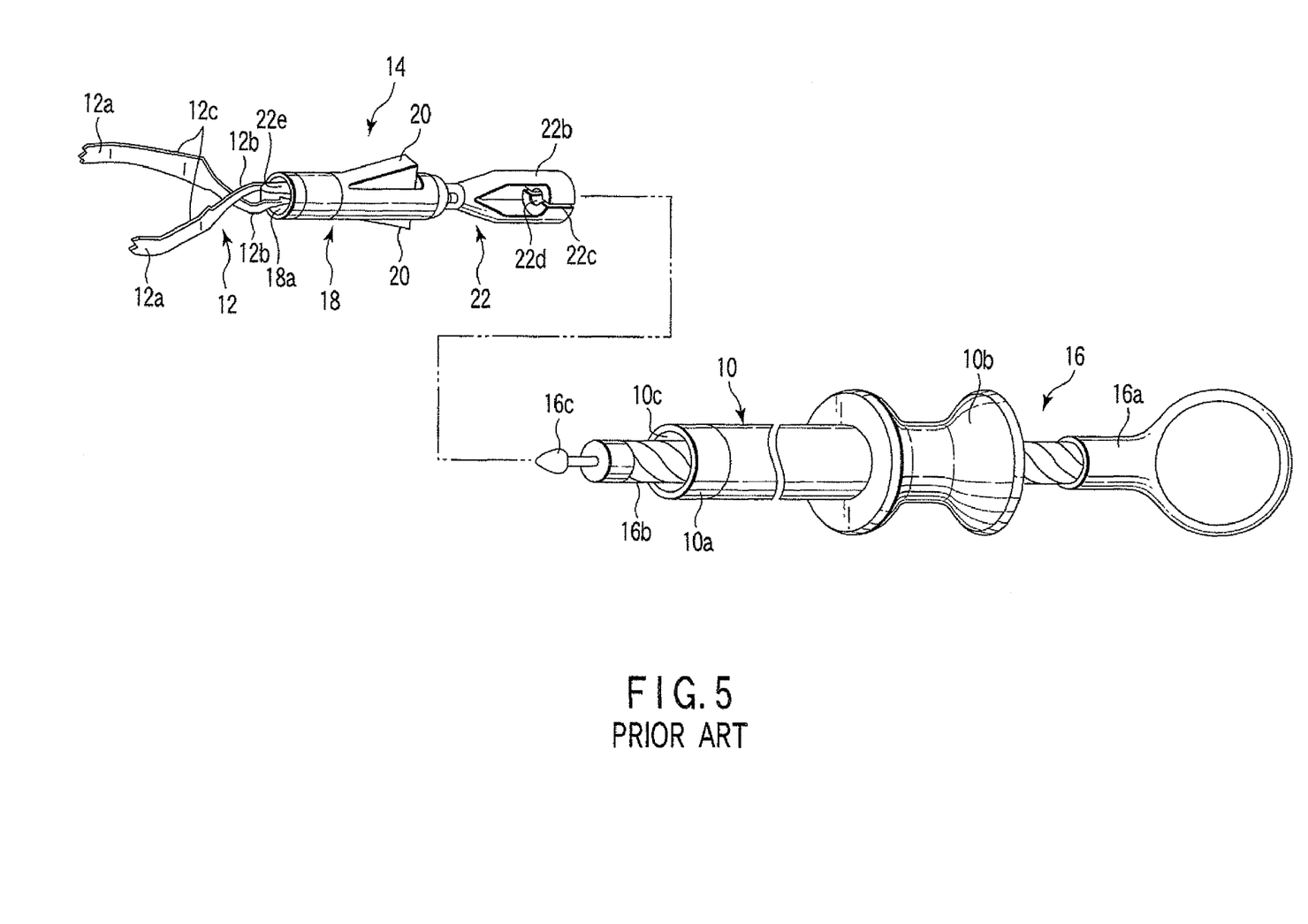
FIG. 5 is a perspective view of a whole conventional clip apparatus for ligaturing a living tissue.

As shown in FIG. 5, an insertion part 10 of a conventional clip apparatus for ligaturing a living tissue includes a distal end portion 10a, a proximal end portion 10b, and a passage 10c extending between the distal end portion 10a and the proximal end portion 10b. The insertion part 10 is inserted into a forceps channel of a not-shown endoscope inserted into a body cavity of a living body, for example a living body, with the distal end portion 10a being as a leading end.

In the above conventional clip apparatus, a clip 12 included in a clip unit 14 provided removably at the distal end portion 10a of the insertion part 10 has slender arms 12c having independent distal ends 12a and other ends 12b connected to each other, and is capable of elastically opening and closing the distal ends 12a.

In the above conventional clip apparatus, a clip operating part 16 being capable of opening and closing the clip 12 of the clip unit 14 includes an external operation portion 16a exposed at the proximal end portion 10b of the insertion part 10 and a clip connecting portion 16b extending in the passage 10c of the insertion part 10 from the external operation portion 16a to the distal end portion 10a of the insertion part 10 and connected to the clip unit 14. And, the clip 12 of the clip unit 14 can be opened and closed by operating the external operation portion 16a.

In the not-shown endoscope, If the insertion part in which the forceps channel is extending does not have flexibility, each of the insertion part 10 and clip operating part 16 of the clip apparatus may not have flexibility. However, if the insertion part of the not-shown endoscope has flexibility, each of the insertion part 10 and clip operating part 16 of the clip apparatus must have flexibility in order to follow curving of the insertion part of the endoscope.

Next, a configuration of the conventional clip unit 14 will be explained with reference to FIGS. 5, 6A and 6B.

The clip unit 14 comprises a clip holding member 18 whose diameter is smaller than that of an opening of the passage 10c in the distal end portion 10a of the insertion part 10. The clip holding member 18 has a clip projecting/retracting passage 18a which extends along a longitudinal center line of the passage 10c and which holds the clip 12 in a projectable/retractable state. When the clip 12 is projected from and retracted into the clip projecting/retracing passage 18a, outside surfaces of the arms 12c of the clip 12 slidingly contact an inner circumferential surface of the clip projecting/retracting passage 18a so that the arms 12c are elastically opened and closed.

The clip unit 14 further comprises engaging portions 20 which are provided around the clip projecting/retracting passage 18a in the clip holding member 18 and which are radially and elastically openable and closable relative to the clip projecting/retracting passage 18a. Each of the engaging portions 20 is slender in a longitudinal direction of the clip projecting/retracting passage 18a. And, only a distal end of the engaging portion 20 in a direction in which the clip holding member 18 projects from the opening of the passage 10c in the distal end portion 10a of the insertion part 10 is connected to a circumferential wall of the clip holding member 18 while the engaging portion 20 excluding the distal end is separated from the circumferential wall of the clip holding member 18. While the clip holding member 18 is retracted in the opening of the passage 10c in the distal end portion 10a of the insertion part 10, each of the engaging portions 20 is pushed by the inner circumferential surface of the passage 10c and elastically bent (that is, closed) about the distal end radially inward relative to the clip projecting/retracting passage 18a. When the clip holding member 18 projects from the opening of the passage 10c, each of the engaging portions 20 is elastically flipped up (that is, opened) around the distal end radially outward relative to the clip projecting/retracing passage 18a. The rear ends of the elastically opened engaging portions 20, located opposite to the distal ends in the longitudinal direction of the clip projecting/retracting passage 18a, engage with a periphery of the opening of the passage 10c in the distal end portion 10a of the insertion part 10 in a direction along the longitudinal center line of the passage 10c, and prevent the clip holding member 18 from retracting into the opening of the passage 10c in the distal end portion 10a of the insertion part 10.

The clip unit 14 further comprises a connecting member 22 which is provided in the clip projecting/retracing passage 18a of the clip holding member 18 and which is movable in the extending direction of the clip projecting/retracing passage 18a. The connecting member 22 is connected to the proximal end portions 12b of the slender arms 12c of the clip 12 and to the clip connecting portion 16b of the clip operating part 16. The connecting member 22 is operated by the clip operating part 16 to move together with the clip 12 in the above described extending direction in the clip projecting/retracing passage 18a. The connecting member 22 has a breakable portion 22a which is broken when a pulling force larger than a predetermined value is applied thereto by the clip operating part 16.

Figure 6A:
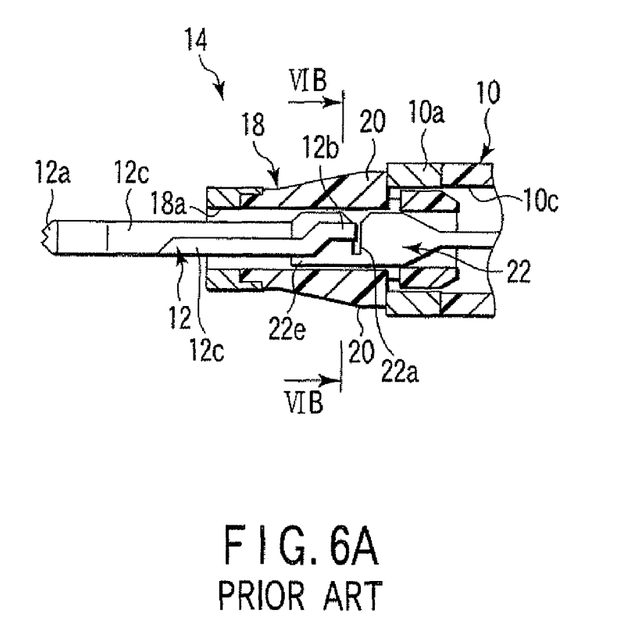
FIG. 6A is an enlarged longitudinal sectional view of a clip unit that is an essential part of the conventional clip apparatus for ligaturing a living tissue shown in FIG. 5.
Figure 6B:
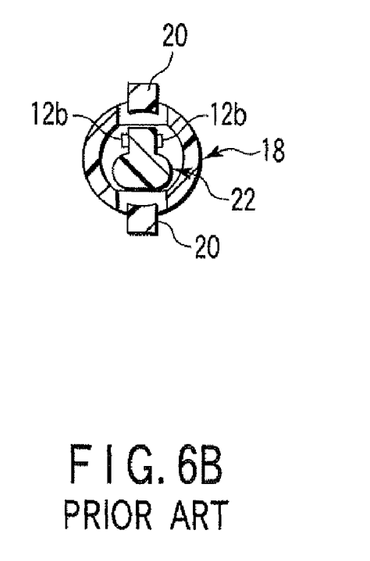
FIG. 6B is a transverse sectional view taken along a line VIB-VIB in FIG. 6A.

In the conventional example shown in FIGS. 5, 6A and 6B, two engaging portions 20 are provided at two positions in the clip holding member 18, the two positions being separated from each other by 180° in a circumferential direction of the clip holding member 18 around the clip projecting/retracting passage 18a. The clip holding member 18 and the two engaging portions 20 are formed as one body by injection molding of synthetic resin with appropriate elasticity and high intensity, such as polyphthalamide (PPA), polyamide (PA), and the like.

The connecting member 22 is formed by injection molding of resin material with high intensity, such as liquid crystal polymer, nylon, and the like. The breakable portion 22a is a cut out which is cut from a part of an outer circumferential surface of the connecting member 22 inwardly in a radial direction of the clip holding member 18 and which extends in a direction crossing the extending direction of the clip projecting/retracting passage 18a. In this cut out, the other ends 12b connected to each other in the slender arms 12c of the clip 12 are hooked.

A proximal end portion 22b of the connecting member 22 is branched into two sections, the proximal end portion 22b being closer to the distal end portion 10a of the insertion part 10 than the breakable portion 22a. Two branched sections are close to each other with a radially extending division line 22c interposed therebetween, and a connection hole 22d extending along the longitudinal center line of the clip projecting/retracting passage 18a is formed in closely facing ends of the branched sections. In the connection hole 22d at the two branched sections of the proximal end portion 22b of the connecting member 22, a substantially conically shaped engaging portion 16c of a projecting end of a projection projecting from the distal end of the clip connecting portion 16b of the clip operating part 16 in the longitudinal direction of the clip operating part 16 is pressed in, so that a rotational connection between the two branched sections of the proximal end portion 22b of the connecting member 22 and the clip connecting portion 16b of the clip operating part 16 is achieved.

A part of the outer circumferential surface of the connecting member 22 is flattened, and a part of the inner circumferential surface of the clip projecting/retracting passage 18a of the clip holding member 18, the part corresponding to the flattened part of the outer circumferential surface of the connecting member 22, is also flattened. The flattened part of the inner circumferential surface of the clip projecting/retracting passage 18a extends in a moving range of the flattened part of the outer circumferential surface of the connecting member 22 while the connecting member 22 moves in the clip projecting/retracting passage 18a. As a result, the connecting member 22 does not rotate in the circumferential direction of the clip projecting/retracting passage 18a in the clip projecting/retracting passage 18a.

A moving path of the breakable part 22a of the connecting member 22 in the clip projecting/extracting passage 18a is adjacent to the inside surface of one of the two engaging portions 20.

Next, a process of ligaturing a desired region of a desired living tissue in a body cavity of a living thing, for example a human body, by using the conventional clip apparatus configured as described above.

First, the insertion part of the not-shown endoscope is inserted into the body cavity, and the distal end of the insertion tube is directed to the desired region of the desired living tissue. Then, the insertion part 10 of the conventional clip apparatus is inserted into the not-shown forceps channel of the endoscope with the distal end portion 10a being as the leading end. In this time, the clip 12 is retracted into the clip projecting/retracting passage 18a of the clip holding member 18, and the clip holding member 18 is retracted into the distal end portion of the passage 10c of the insertion part 10.

After the distal end portion 10a of the insertion part 10 is projected from the distal end opening of the forceps channel of the insertion part of the endoscope, the external operation portion 16a of the clip operating part 16 is pushed to project the clip holding member 18 from the distal end portion of the passage 10c of the insertion part 10 and to project the clip 12 from the clip projecting/retracing passage 18a of the clip holding member 18.

Figure 7A:
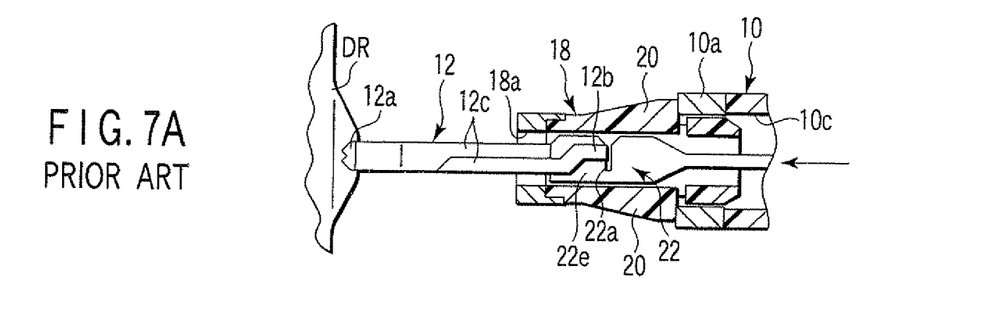
FIGS. 7A, 7B, 7C and 7D are longitudinal section views showing sequential steps of an operation for ligaturing a desired region of a desired living tissue in a body cavity of a living thing by using the clip unit of the clip apparatus shown in FIGS. 6A and 6B.

Each of the two engaging portions 20 of the projected clip holding member 18 is elastically flipped up (that is, opened) around its distal end outward in the radial direction of the clip holding member 18, as shown in FIG. 7A. The rear ends of the opened engaging portions 20 are engaged with the periphery of the opening of the passage 10c in the distal end portion 10a of the insertion part 10 in the direction along the longitudinal center line of the passage 10c, and prevent the clip holding member 18 from retracting into the opening of the passage 10c in the distal end portion 10a of the insertion part 10.

As shown in FIG. 7A, the projected clip 12 opens the arms 12c around the other ends 12b outward in the radial direction of the clip projecting/retracing passage 18a. Thereafter, in order to locate the gap between the opened distal ends 12a of the arms 12c of the clip 12 on the desired region DR of the desired living tissue in the body cavity of the living thing, for example the human body, the direction of the distal end portion of the insertion part of the not-shown endoscope (that is, the direction of the distal end portion 10a of the insertion part 10) and the push amount of the external operation portion 16a of the clip operating part 16 directing the proximal end portion 10b of the insertion part 10 (that is, the projecting distance of the clip 12 from the clip projecting/retracting passage 18a of the clip holding member 18) are adjusted.

Then, after the external operation portion 16a is pushed to make the opened distal ends 12a of the arms 12c of the clip 12 bite the desired region DR of the desired living tissue, the external operation portion 16a is pulled while holding the proximal end portion 10b of the insertion part 10 not to move the insertion part 10 in its longitudinal direction. As a result, while the arms 12c of the clip 12 are pulled into the clip projecting/retracting passage 18a of the clip holding member 18, the outside surfaces of the arms 12c slidingly contact the periphery of the opening of the clip projecting/retracing passage 18a at the projecting end of the clip holding member 18 and are pushed inward in the radial direction of the opening, so that the distal ends 12a of the arms 12c of the clip 12 can hold the desired region DR of the desired living tissue, as shown in FIG. 7B.

By pulling the external operation portion 16a furthermore, a pulling resistance generated in the desired region DR of the desired living tissue and a frictional resistance generated on the outside surface of the arms 12c of the clip 12 with respect to the periphery of the opening of the clip projecting/retracing passage 18a are increased, so that the pulling force applied to the base of the breakable portion 22a of the connecting member 22 by the clip operating part 16 gets close to a predetermined value at which the base of the breakable portion 22a is to be broken.

Figure 7B:
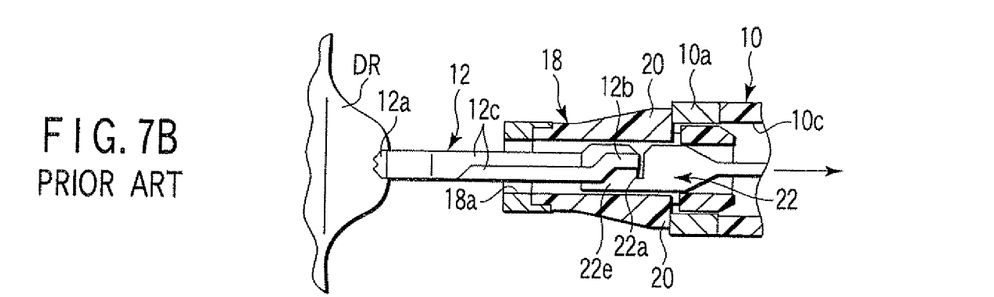
Figure 7C:
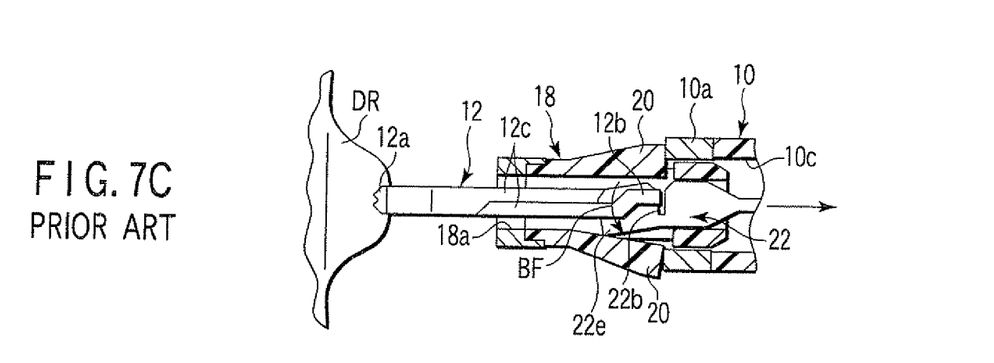

Just before the base of the breakable portion 22a of the connecting member 22 is broken, a deviating force BF around the base is applied to a distal end portion 22e of the connecting member 22, as shown in FIG. 7C.

In a case that the opening distance of the distal ends 12a of the arms 12c of the clip 12 is relative large when the opened distal ends 12a of the arms 12c of the clip 12 bites the desired region DR of the desired living tissue as shown in FIG. 7B, the deviating force BF around the base is applied to the distal end portion 22e of the connecting member 22 as shown in FIG. 7C before the arms 12c of the clip 12 are sufficiently pulled into the clip projecting/retracting passage 18a of the clip holding member 18.

Figure 7D:
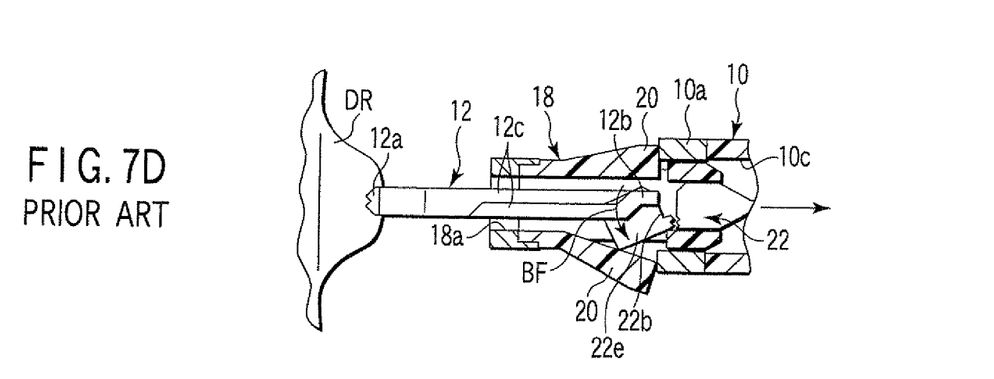

In this time, the distal end portion 22e of the connecting member 22 faces the inside surface of one of the two engaging portions 20 of the clip holding member 18 in the clip projecting/retracing passage 18a. Therefore, the distal end portion 22e of the connecting member 22 to which the deviating force BF is applied pushes the inside surface of the engaging portion 20 corresponding to the distal end portion 22e of the connecting member 22 outward in the radial direction of the clip projecting/retracting passage 18a, until the base of the breakable portion 22a of the connecting member 22 is broken as shown in FIG. 7D.

As a result, the arms 12c of the clip 12 are prevented from being pulled furthermore into the clip projecting/retracting passage 18a of the clip holding member 18, so that the bite of the distal ends 12a of the arms 12 of the clip 12 in the desired region DR of the desired living tissue (that is, the ligaturing of the desired region DR of the desired living tissue) is left insufficiently.

Figure 8A:
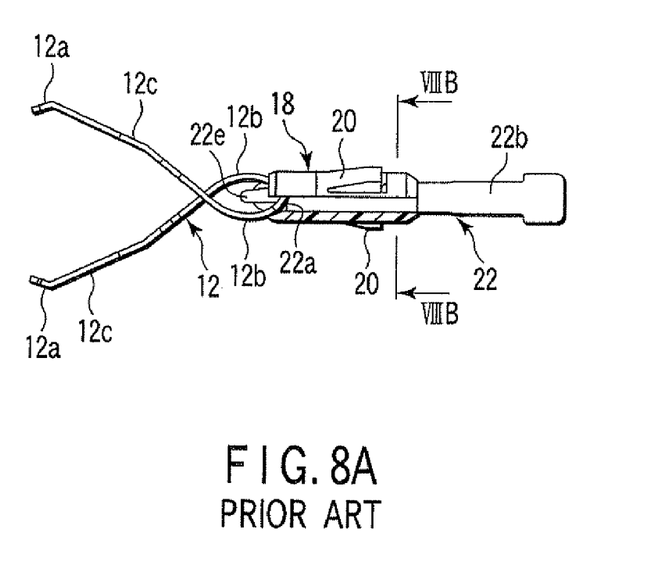
FIG. 8A is a half sectional view of a clip unit that is an essential part of another conventional clip apparatus for ligaturing a living tissue.
Figure 8B:
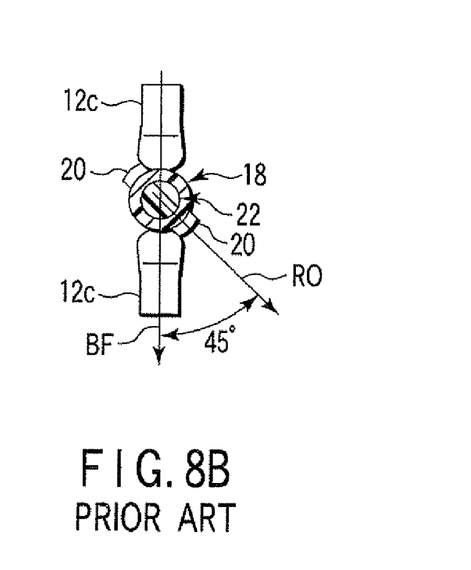
FIG. 8B is a transverse sectional view taken along a line VIIIB-VIIIB in FIG. 5A.

In addition to the conventional clip apparatus described above with reference to FIGS. 5 to 7D, another conventional clip apparatus is known. The other conventional clip apparatus is only different from the above described conventional clip apparatus in that a direction RO in which the engaging portion 20 close to the base of the breakable portion 22a of the connecting member 22 in the clip holding member 18 bends elastically is displaced in the circumferential direction of the clip holding member 18 by 45° from a direction in which the deviating force BF around the base applied to the distal end portion 22e of the connecting member 22 just before the base of the breakable portion 22a of the connecting member 22 is broken, as shown in FIGS. 8A and 8B.

Even in such the other conventional clip apparatus, the same problems as that occurred in the conventional clip apparatus described above with reference to FIGS. 5 to 7D are occurred.

BRIEF SUMMARY OF THE INVENTION

A clip apparatus for ligaturing a living tissue according to one aspect of this invention comprises: an insertion part which includes a distal end portion, a proximal end portion and a passage extending between the distal end portion and the proximal end portion and which is inserted into a forceps channel of an endoscope inserted into a body cavity of a living thing with the distal end portion being a leading end; a clip unit which is removably provided in the distal end portion of the insertion part and which includes a clip having slender anus having independent distal ends and proximal ends connected to each other, the clip being capable of elastically opening and closing the distal ends; and a clip operating part which includes an external operation portion exposed at the proximal end portion of the insertion part and a clip connecting portion extending in the passage of the insertion part from the external operation portion to the distal end portion and connected to the clip unit and which is configured to open and close the clip of the clip unit by operating the external operation portion.

The clip unit includes: a clip holding member which has a diameter smaller than that of the opening of the passage in the distal end portion of the insertion part and a clip projecting/retracting passage extending along a longitudinal center line of the passage, holding the clip to be capable of projecting and retracting the clip, and elastically opening and closing the arms of the clip by projecting and retracting of the clip; an engaging portion which is provided around the clip projecting/retracting passage in the clip holding member and which is elastically openable and closable in a radial direction of the clip projecting/retracting passage, the engaging portion being pushed by an inner circumferential surface of the passage and elastically closed while the clip holding member is retracted in the opening of the passage in the distal end portion of the insertion part, and elastically opened when the clip holding member projects from the opening of the passage and engaging with a periphery of the opening of the passage in the distal end portion of the insertion part in a direction along the longitudinal center line of the passage; a connecting member which is provided in the clip projecting/retracting passage of the clip holding member to be movable in an extending direction of the clip projecting/retracting passage, which is connected to the proximal ends of the arms and the clip connecting portion of the clip operating part to move together with the clip in the clip projecting/retracting passage in the extending direction by operating the clip operating part, and which has a breakable portion and a distal end portion closer to the clip than the breakable portion, the breakable portion being to be broken when a pulling force higher than a predetermined value is applied by the clip operating part; and an engaging portion excessive opening preventing structure which prevents excessive opening of the engaging portion by a deviating force directed outward in the radial direction and applied to the distal end portion of the connecting member as the breakable portion of the connecting member is broken.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
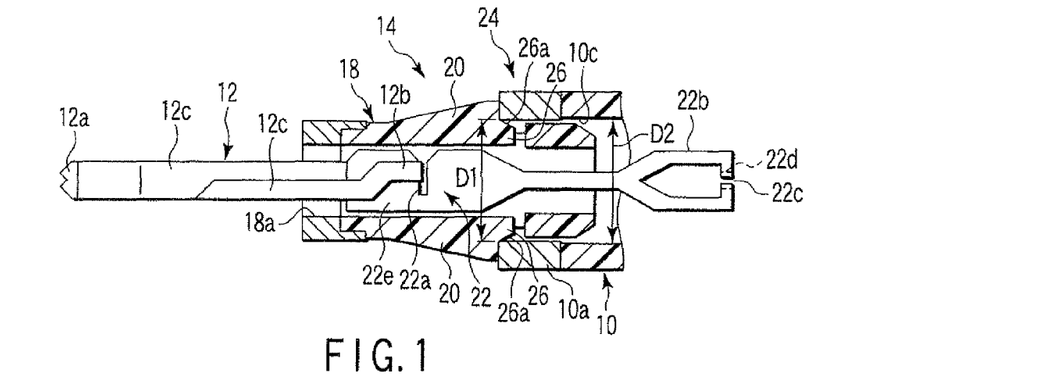
FIG. 1 is an enlarged longitudinal sectional view of a clip unit that is an essential part of a clip apparatus for ligaturing a living tissue according to a first embodiment of the present invention.

A configuration of a clip apparatus for ligaturing a living tissue according to a first embodiment of the invention will be explained hereinafter with reference to FIG. 1.

Most of the structural elements of the clip apparatus for ligaturing a living tissue according to the first embodiment are the same as those of the conventional clip apparatus for ligaturing a living tissue already described with reference to FIGS. 5, 6A and 6B. Therefore, the structural elements of the clip apparatus for ligaturing a living tissue according to the first embodiment, which are the same as those of the conventional clip apparatus for ligaturing a living tissue described with reference to FIGS. 5, 6A and 6B, are denoted by the same reference numerals as those denoting the same structural elements of the conventional clip apparatus for ligaturing a living tissue, and detailed description of these structural elements will be omitted.

The configuration of the clip apparatus according to the first embodiment is different from that of the conventional clip apparatus in that the clip apparatus according to the first embodiment is provided with an engaging portion excessive opening preventing structure 24. The excessive opening preventing structure 24 prevents excessive opening of the engaging portion 20 caused by the deviating force BF (refer to FIG. 7C) applied to the portion closer to the clip 12 than the breakable portion 22a (namely, the distal end portion 22e) in the connecting member 22 when the breakable portion 22a of the connecting member 22 is broken and directing outward in the radial direction of the clip projecting/retracing passage 18a.

Specifically, the engaging portion excessive opening preventing structure 24 in this embodiment includes an opening restriction portion 26 which is provided in the engaging portion 20, which has a facing region 26 facing a part adjacent to the opening of the passage 10c in the distal end portion 10a of the insertion part 10 while the engaging portion 20 is elastically opened, and which restricts the opening of the engaging portion 20. The facing region 26a of the opening restriction portion 26 is configured by a slope inclined inward in a radial direction of the passage 10c of the insertion part 10 as separating from the opening along the extending direction of the passage 10c.

The opening restriction portion 26 is formed by injection molding of the same material as that of the engaging portion 20, or the clip holding member 18, simultaneously with the engaging portion 20 and clip holding member 18. A maximum distance D1 between the two facing regions 26a of the two engaging portions 20 in the radial direction of the passage 10c of the insertion part 10 is the same as or slightly smaller than the diameter D2 of the passage 10c of the insertion part 10.

Next, an operation for ligaturing a desired region of a desired living tissue in a body cavity of a living thing, for example a human body, by using the clip apparatus according to the first embodiment of the invention configured as described above.

First, an insertion part of a not-shown endoscope is inserted into the body cavity, and a distal end of the insertion part is directed to the desired region of the living tissue. Next, the insertion part 10 (refer to FIG. 5) of the clip apparatus is inserted into a not-shown forceps channel of the endoscope with the distal end portion 10a being a leading end. In this time, the clip 12 is retracted into the clip projecting/retracting passage 18a of the clip holding member 18, and the clip holding member 18 is retracted into the distal end portion of the passage 10c of the insertion part 10.

After the distal end portion 10a of the insertion part 10 is projected from the distal end opening of the forceps channel of the insertion part of the endoscope, the external operation portion 16a (refer to FIG. 5) of the clip operating part 16 is pushed to project the clip holding member 18 from the distal end portion of the passage 10c of the insertion part 10, and the clip 12 is projected from the clip projecting/retracing passage 18a of the clip holding member 18.

Figure 2A:
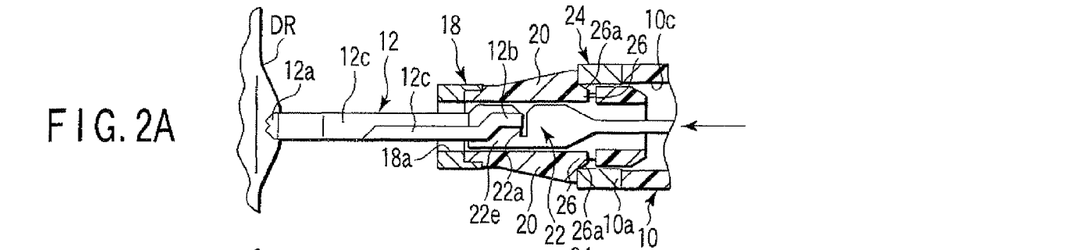
FIGS. 2A, 2B, 2C and 2D are longitudinal section views showing sequential steps of an operation for ligaturing a desired region of a desired living tissue in a body cavity of a living thing by using the clip unit of the clip apparatus of FIG. 1.

Each of the two engaging portions 20 of the projected clip holding member 18 is elastically flipped up (opened) outward about its distal end in the radial direction of the clip holding member 18, as shown in FIG. 2A. The rear ends of the opened engaging portions 20 engage with the periphery of the opening of the passage 10c in the distal end portion 10a of the insertion part 10 in a direction along the longitudinal center line of the passage 10c, and prevent the clip holding member 18 from retracting into the opening of the passage 10c in the distal end portion 10a of the insertion part 10. At the same time, the inclined facing region 26a of the opening restriction portion 26 formed as one body with the engaging portion 20 faces the part adjacent to the opening of the passage 10c in the distal end portion 10a of the insertion part 10.

The maximum distance D1 between the two facing regions 26a of the two engaging portions 20 in the radial direction of the passage 10c of the insertion part 10 is the same as or slightly smaller than the diameter D2 of the passage 10c of the insertion part 10. Further, the facing region 26a of the opening restriction portion 26 is configured by the slope inclined inward in the radial direction of the passage 10c as separating from the opening along the extending direction of the passage 10c of the insertion part 10.

Therefore, the two opening restriction portions 26 of the two engaging portions 20 allows the rear ends of the two opened engaging portions 20 to engage with a periphery of the opening of the passage 10c in the distal end portion 10a of the insertion part 10 in a direction along the longitudinal center line of the passage 10c, so that the clip holding member 18 is prevented from entering into the opening of the passage 10c in the distal end portion 10a of the insertion part 10. This means that correct positioning of the clip holding member 18 to the distal end of the distal end portion 10a of the insertion part 10 is not prevented by the two opening restriction portions 26 of the two engaging portions 20.

As shown in FIG. 2A, the arms 12c of the projected clip 12 are opened about the other ends 12b outward in the radial direction of the clip projecting/retracting passage 18a. Thereafter, in order to locate a gap between the opened distal ends 12a of the arms 12c of the clip 12 to the desired region DR of the desired living tissue in the body cavity of the living things, for example the human body, the direction of the distal end portion of the insertion part of the not-shown endoscope (that is, the direction of the distal end portion 10a of the insertion part 10) and the push amount of the external operation portion 16a of the clip operating part 16 toward the proximal end portion 10b of the insertion part 10 (e.g., the projecting distance of the clip 12 from the clip projecting/retracting passage 18a of the clip holding member 18) are adjusted.

Then, after the external operation portion 16a is further pushed to make the opened distal ends 12a of the arms 12c of the clip 12 bite the desired region DR of the desired living tissue, the external operation portion 16a is pulled while holding the proximal end portion 10b of the insertion part 10 not to move the insertion part 10 in its longitudinal direction. As a result, while the arms 12c of the clip 12 are pulled into the clip projecting/retracting passage 18a of the clip holding member 18, the outside surfaces of the arms 12c slidingly contact the periphery of the opening of the clip projecting/retracing passage 18a at the projection end of the clip holding member 18, so that the arms 12c are pushed inward in the radial direction of the opening and the distal ends 12a of the arms 12c of the clip 12 can hold the desired region DR of the desired living tissue, as shown in FIG. 2B.

By further pulling the external operation portion 16a, a pulling resistance generated in the desired region DR of the desired living tissue and a frictional resistance generated on the outside surfaces of the arms 12c of the clip 12 to the periphery of the opening of the clip projecting/retracing passage 18a are increased, so that a pulling force applied from the clip operating portion 16 to the base of the breakable portion 22a of the connecting member 22 gets close to a predetermined value to break the base.

Figure 2B:
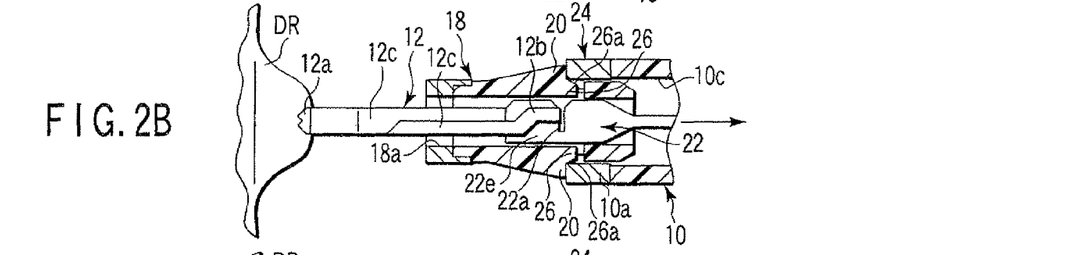
Figure 2C:
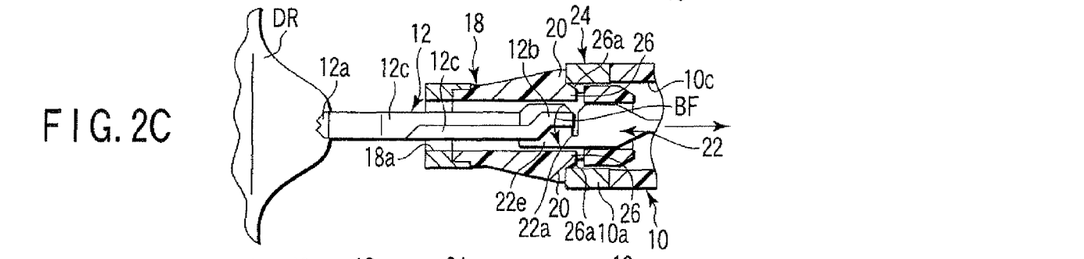

Just before the base of the breakable portion 22a of the connecting member 22 is broken, a deviating force BF around the base is applied to the distal end portion 22e of the connecting member 22, as shown in FIG. 2C.

In a case that the opening distance of the distal ends 12a of the arms 12c of the clip 12 is relative large when the opened distal ends 12a of the arms 12c of the clip 12 bites the desired region DR of the desired living tissue as shown in FIG. 2B, the deviating force BF around the base is applied to the distal end portion 22e of the connecting member 22 as shown in FIG. 2C, before the arms 12c of the clip 12 are sufficiently pulled into the clip projecting/retracting passage 18a of the clip holding member 18.

In this time, the distal end portion 22e of the connecting member 22 faces the inside surface of one of the two engaging portions 20 of the clip holding member 18 in the clip projecting/retracting passage 18a. Therefore, the distal end portion 22e of the connecting member 22 to which the deviating force BF is applied pushes the inside surface of the engaging portion 20 corresponding to the distal end portion 22e outward in the radial direction of the clip projecting/retracting passage 18a, until the base of the breakable portion 22a of the connecting member 22 is broken.

However, since the inclined facing region 26a of the opening restriction portion 26 formed as one body with the one engaging portion 20 contacts the part adjacent to the opening of the passage 10c in the distal end portion 10a of the insertion part 10, the one engaging portion 20 resists the deviating force BE applied from the distal end portion 22e of the connecting member 22 and does not open furthermore.

Figure 2D:
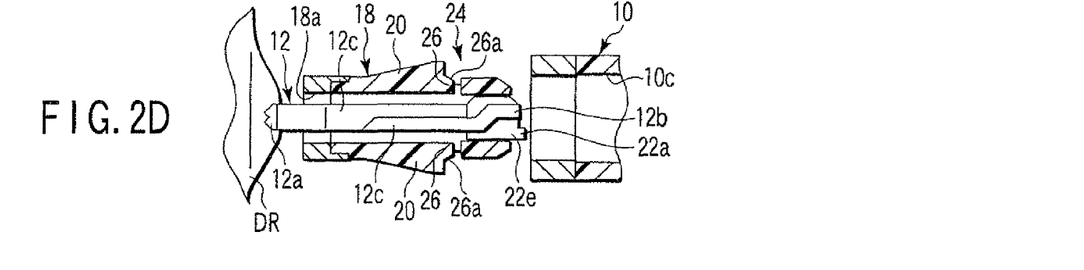

As a result, retraction of the arms 12c of the clip 12 into the clip projecting/retracting passage 18a of the clip holding member 18 is not stopped until the base of the breakable portion 22a of the connecting member 22 is completely broken. When the base of the breakable portion 22a of the connecting member 22 is completely broken, the arms 12c of the clip 12 are sufficiently pulled into the clip projecting/retracting passage 18a of the clip holding member 18, as shown in FIG. 2D.

Therefore, after the base of the breakable portion 22a of the connecting member 22 is completely broken, the arms 12c of the clip 12 are sufficiently pulled into the clip projecting/retracting passage 18a of the clip holding member 18 so that the clip 12 biting (ligaturing) strongly the desired region DR of the desired living tissue by the distal ends 12a of the arms 12c is left in the body cavity together with the clip holding member 18 and the distal end portion 22e of the connecting member 22.

Second Embodiment

Figure 3:
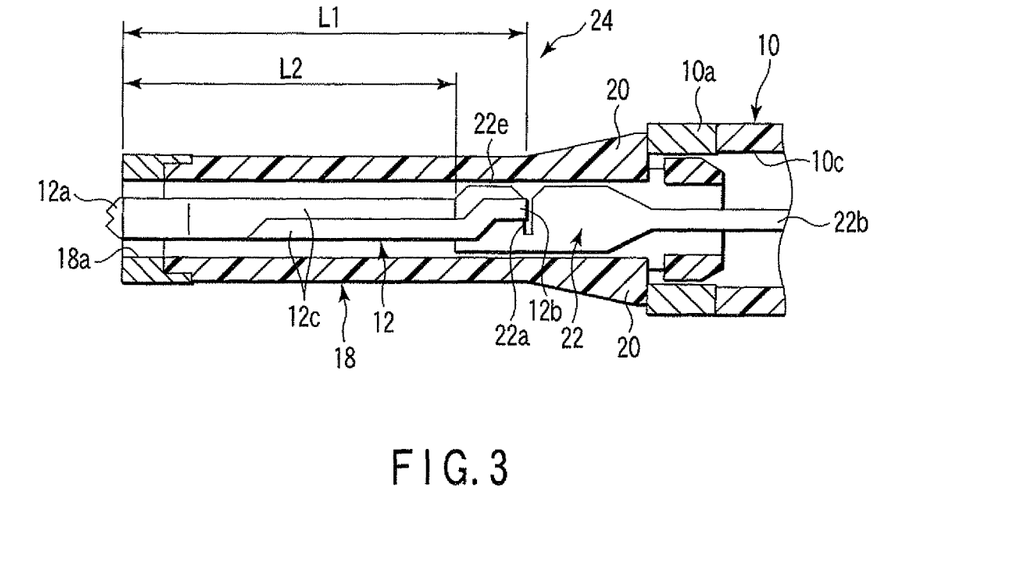
FIG. 3 is an enlarged longitudinal sectional view of a clip unit that is an essential part of a clip apparatus for ligaturing a living tissue according to a second embodiment of the invention.

Next, a configuration of a clip apparatus for ligaturing a living tissue according to a second embodiment of the invention will be explained hereinafter with reference to FIG. 3.

Most of the structural elements of the clip apparatus for ligaturing a living tissue according to the second embodiment are the same as those of the conventional clip apparatus for ligaturing a living tissue already described with reference to FIGS. 5, 6A and 6B. Therefore, the structural elements of the clip apparatus for ligaturing a living tissue according to the second embodiment, which are the same as those of the conventional clip apparatus for ligaturing a living tissue described with reference to FIGS. 5, 6A and 6B, are denoted by the same reference numerals as those denoting the same structural elements of the conventional clip apparatus for ligaturing a living tissue, and detailed description of these structural elements will be omitted.

The configuration of the clip apparatus according to the second embodiment is different from that of the conventional clip apparatus in that the clip apparatus according to the second embodiment is provided with an engaging portion excessive opening preventing structure 24. The excessive opening preventing structure 24 prevents excessive opening of the engaging portion 20 caused by the deviating force BF (refer to FIG. 7C) applied to the portion closer to the clip 12 than the breakable portion 22a (namely, the distal end portion 22e) in the connecting member 22 when the breakable portion 22a of the connecting member 22 is broken and directing outward in the radial direction of the clip projecting/retracing passage 18a.

Specifically, the engaging part excessive opening prevention structure 24 in this embodiment includes a setting of a distance L1 from a clip projecting/retracting opening of the clip projecting/retracting passage 18a of the clip holding member 18 to a distal end of the engaging portion 20 (the distal end of the engaging portion 20 is located in a side of the clip projecting/retracting opening of the clip projecting/retracting passage 18a) longer than a distance L2 from the distal ends 12a of the arms 12c of the clip 12 to the distal end of the distal end portion 22e located closer to the distal ends 12a of the clip 12 than the breakable portion 22a in the connecting member 22.

The clip 12 pushed by the clip operating member 16 (refer to FIG. 5) to hold the desired region DR of the desired living tissue projects the arms 12c from the distal end opening of the clip projecting/retracing passage 18a of the clip holding member 18, and the distal ends 12a of the arms 12c are pressed on an area around the desired region DR of the desired living tissue, as shown in FIG. 2A.

Thereafter, the clip 12 is pulled by the clip operating member 16 (refer to FIG. 5) and the arms 12c of the clip 12 are pulled into the clip projecting/retracting passage 18a of the clip holding member 18. In this time, the outside surfaces of the arms 12c of the clip 12 slidingly contact the periphery of the opening of the clip projecting/retracting passage 18a at the projected end of the clip holding member 18, so that the arms 12c are pushed inward in the radial direction of the above opening and the distal ends 12a of the arms 12c of the clip 12 can hold the desired region DR of the desired living tissue, as shown in FIG. 2B.

While the external operation portion 16a is pulled furthermore, a pulling resistance generated in the desired region DR of the desired living tissue and a frictional resistance generated on the outside surfaces of the arms 12c of the clip 12 to the periphery of the opening of the clip projecting/retracing passage 18a are increased, so that the pulling force applied to the base of the breakable portion 22a of the connecting member 22 by the clip operating portion 16 gets close to the predetermined value to break the base.

Just before the base of the breakable portion 22a of the connecting member 22 is broken, a deviating force BF around the base is applied to the distal end portion 22e of the connecting member 22, as shown in FIG. 2C.

However, in this time, the distal end of the distal end portion 22e of the connecting member 22 does not reach a position corresponding to the distal end of one of two engaging portions 20 of the clip holding member 18 in the clip projecting/retracting passage 18a.

The base of the breakable portion 22a of the connecting member 22 is completely broken before the distal ends 12a of the arms 12c of the clip 12 holding the desired region DR of the desired living tissue reaches the opening of the clip projecting/retracting passage 18a at the projected end of the clip holding member 18 (that is, before the distal end of the distal end portion 22e located closer to the distal ends 12a of the clip 12 than the breakable portion 22a in the connecting member 22 reaches the distal ends of the two engaging portions 20 of the clip holding member 18).

As described before, by the engaging part excessive opening preventing structure 24 in this embodiment, the distance L1 from the clip projecting/retracting opening in the clip projecting/retracting passage 18a of the clip holding member 18 to the end of the engaging portion 20 located in the side of the clip projecting/retracting opening (that is, the distal end of the engaging portion 20) is set longer than the distance L2 from the distal ends 12a of the arms 12c of the clip 12 to the distal end of the distal end portion 22e located closer to the distal ends of the clip 12 than the breakable portion 22a in the connecting member 22.

Therefore, until the base of the breakable portion 22a of the connecting member 22 is broken, the distal end of the distal end portion 22e of the connecting member 22 to which the deviating force BF is applied slidingly contacts an area on the inner circumferential surface of the clip projecting/retracting passage 18a located closer to the projected end of the clip holding member 18 than the distal ends of the two engaging portions 20. This means that, until the base of the breakable portion 22a of the connecting member 22 is broken, the distal end of the distal end portion 22e of the connecting member 22 to which the deviating force BF is applied does not push the inside surface of the corresponding engaging portion 20 outward in the radial direction of the clip projecting/retracting passage 18a.

As a result, the retraction of the arms 12c of the clip 12 into the clip projecting/retraction passage 18a of the clip holding member 18 is not stopped until the base of the breakable portion 22a of the connecting member 22 is completely broken. When the base of the breakable portion 22a of the connecting member 22 is completely broken, the arms 12c of the clip 12 are sufficiently pulled into the clip projecting/retracting passage 18a of the clip holding member 18, as shown in FIG. 2D.

Therefore, after the base of the breakable portion 22a of the connecting member 22 is completely broken, the arms 12c of the clip 12 are sufficiently pulled into the clip projecting/retracting passage 18a of the clip holding member 18, so that the clip 12 biting (ligaturing) strongly the desired region DR of the desired living tissue by the distal ends 12a of the arms 12c is left in the body cavity together with the clip holding member 18 and the distal end portion 22e of the connecting member 22, as shown in FIG. 2D.

Third Embodiment

Next, a configuration of a clip apparatus for ligaturing a living tissue according to a third embodiment of the invention will be explained hereinafter with reference to FIGS. 4A and 4B.

Most of the structural elements of the clip apparatus for ligaturing a living tissue according to the third embodiment are the same as those of the conventional clip apparatus for ligaturing a living tissue already described with reference to FIGS. 5, 6A and 6B. Therefore, the structural elements of the clip apparatus for ligaturing a living tissue according to the third embodiment, which are the same as those of the conventional clip apparatus for ligaturing a living tissue described with reference to FIGS. 5, 6A and 6B, are denoted by the same reference numerals as those denoting the same structural elements of the conventional clip apparatus for ligaturing a living tissue, and detailed description of these structural elements will be omitted.

The configuration of the clip apparatus according to the third embodiment is different from that of the conventional clip apparatus in that the clip apparatus according to the third embodiment is provided with an engaging portion excessive opening preventing structure 24. The excessive opening preventing structure 24 prevents excessive opening of the engaging portion 20 caused by the deviating force BF (refer to FIG. 7C) applied to the portion closer to the clip 12 than the breakable portion 22a (namely, the distal end portion 22e) in the connecting member 22 when the breakable portion 22a of the connecting member 22 is broken and directing outward in the radial direction of the clip projecting/retracing passage 18a.

Figure 4A:
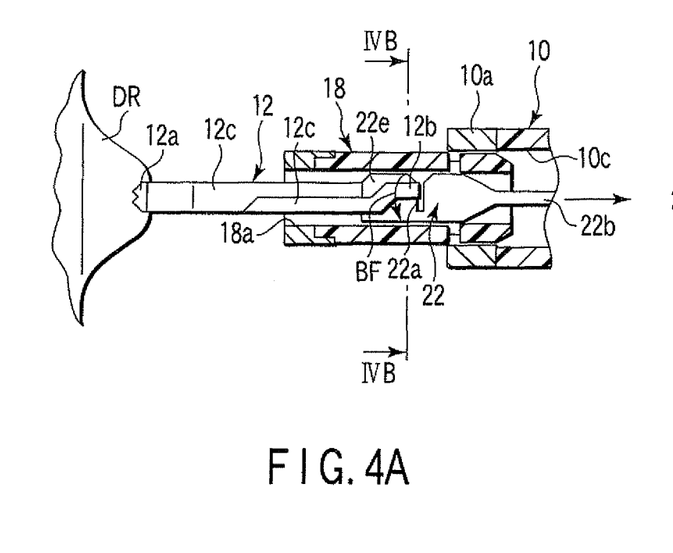
FIG. 4A is an enlarged longitudinal sectional view of a clip unit that is an essential part of a clip apparatus for ligaturing a living tissue according to a third embodiment of the invention.
Figure 4B:
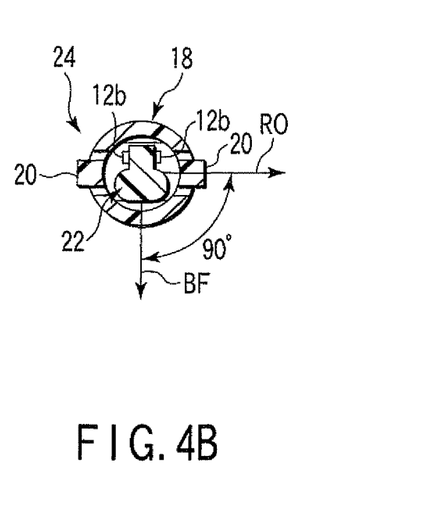
FIG. 4B is a transverse sectional view taken along a line IVB-IVB in FIG. 4A.

Specifically, the engaging part excessive opening preventing structure 24 in this embodiment, as shown in FIG. 4B, includes separating and making independent an opening/closing direction RO of the engaging portion 20 and a direction in which the deviating force BF directs from and of the each other in a circumferential position around the extending direction of the clip projecting/retracting passage 18a. In this embodiment, the opening/closing direction RO of the engaging portion 20 and the direction in which the deviating force BF directs are separated from each other by 90° in the circumferential position around the extending direction of the clip projecting/retracting passage 18a and independent of each other.

The clip 12 pushed by the clip operating member 16 (refer to FIG. 5) to hold the desired region DR of the desired living tissue projects the arms 12c of the clip 12 from the distal end opening of the clip projecting/retracing passage 18a of the clip holding member 18, and the distal ends 12a of the arms 12c are pressed on an area around the desired region DR of the desired living tissue, as shown in FIG. 2A.

Thereafter, the arms 12c of the clip 12 are pulled into the clip projecting/retracting passage 18a of the clip holding member 18 by the clip operating member 16 (refer to FIG. 5), and the outside surfaces of the arms 12c of the clip 12 slidingly contact the periphery of the opening of the clip projecting/retracting passage 18a at the projected end of the clip holding member 18 so that the arms 12c are pushed inward in the radial direction of the above opening and the distal ends 12a of the arms 12c of the clip 12 can hold the desired region DR of the desired living tissue, as shown in FIG. 2B.

When the external operation portion 16a is pulled furthermore, a pulling resistance generated in the desired region DR of the desired living tissue and a frictional resistance generated on the outside surfaces of the arms 12c of the clip 12 to the periphery of the opening of the clip projecting/retracing passage 18a are increased so that the pulling force applied to the base of the breakable portion 22a of the connecting member 22 by the clip operating part 16 gets close to the predetermined value to break the base.

Just before the base of the breakable portion 22a of the connecting member 22 is broken, the deviating force BF around the base is applied to the distal end portion 22e of the connecting member 22, as shown in FIG. 4A.

However, in this embodiment, the opening/closing direction RO of the engaging portion 20 and the direction in which the deviating force BF directs are separated from each other in the circumferential position around the extending direction of the clip projecting/retracting passage 18a and independent of each other. Therefore, in this time, the distal end portion 22e of the connecting member 22 does not face the inside surface of any of the two engaging portions 20 of the clip holding member 18 in the clip projecting/retracting passage 18a.

This means that, until the base of the breakable portion 22a in the connecting member 22 is broken, the distal end of the distal end portion 22e of the connecting member 22 to which the deviating force BF is applied does not push the inside surface of any of the two engaging portions 20 outward in the radial direction of the clip projecting/retracting passage 18a.

As a result, the retraction of the arms 12c of the clip 12 into the clip projecting/retracting passage 18a of the clip holding member 18 is not stopped until the base of the breakable portion 22a in the connecting member 22 is completely broken. When the base of the breakable portion 22a in the connecting member 22 is completely broken, the arms 12c of the clip 12 are sufficiently pulled into the clip projecting/retracting passage 18a of the clip holding member 18, as shown in FIG. 2D.

Therefore, after the base of the breakable portion 22a in the connecting member 22 is completely broken, the arms 12c of the clip 12 are sufficiently pulled into the clip projecting/retracting passage 18a of the clip holding member 18 so that the clip 12 biting (ligaturing) strongly the desired region DR of the desired living tissue by the distal ends 12a of the arms 12c is left in the body cavity together with the clip holding member 18 and the distal end portion 22e of the connecting member 22, as shown in FIG. 2D.

In this embodiment, the opening/closing direction RO of the engaging portion 20 and the direction in which the deviating force BF directs are separated from each other by 90° in the circumferential position around the extending direction of the clip projecting/retracting passage 18a and independent of each other, in order to separate the opening/closing direction RO of the engaging portion 20 and the direction in which the deviating force BF directs from each other an to make them independent of each other in the circumferential position around the extending direction of the clip projecting/retracting passage 18a. However, in order to separate the opening/closing direction RO of the engaging portion 20 and the direction in which the deviating force BF directs from each other and making them independent of each other in the circumferential position around the extending direction of the clip projecting/retracting passage 18a, the opening/closing direction RO of the engaging portion 20 and the direction in which the deviating force BF directs may be separated over 45° in the circumferential position around the extending direction of the clip projecting/retracting passage 18a.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A clip apparatus for ligaturing a living tissue, comprising:

an insertion part which can be inserted into a forceps channel of an endoscope inserted into a body cavity of a living tissue, and which includes a longitudinally extending passage extending along a longitudinal direction thereof;

a clip unit which includes a clip having slender arms capable of elastically opening and closing distal end portions thereof around mutually connected proximal ends thereof, and which can be projected from and retracted into the passage of the insertion part through an opening at a distal end portion of the insertion part; and a clip operating part which extends in the passage of the insertion part, which includes an external operation portion exposed at a proximal end portion of the insertion part and a clip connecting portion connected to the clip unit, and which operates the projection and retraction of the clip by the external operation portion;

the clip unit including:

a clip holding member which is housed in the passage of the insertion part to project from and to be retracted into the passage through the opening at the distal end portion, and which has a clip projecting/retracting passage in which the clip is housed to project from and to be retracted into the clip projecting/retracting passage so that the slender arms of the clip open and close the distal end portions thereof elastically;

an engaging portion, which is cut out from a circumferential wall of the clip holding member to be connected only at its one end to the circumferential wall of the clip holding member, which can open and close elastically around the one end thereof in a radial direction of the clip projecting/retracting passage between an open position and a closed position, and which opens and closes elastically by the projection and retraction of the clip holding member from and into the passage of the insertion part, a rear end of the engaging portion engaging with an end of the distal end portion of the insertion part to prevent the retraction of the clip holding member into the passage through the opening at the distal end portion of the insertion part while the engaging portion opens at the open position, and a connecting member which is movably housed in the clip projecting/retracting passage of the clip holding member, which has a distal end portion, a proximal end portion, and a breakable portion between the distal end portion and the proximal end portion, the distal end portion being connected to the proximal ends of the clip, the proximal end portion being connected to the clip connecting portion of the clip operating part, and the breakable portion being off to and in parallel with a longitudinal center line of the clip projecting/retracting passage in the radial direction of the clip projecting/retracting passage, and in which a deviating force is generated in the distal end portion to direct the distal end portion outward in the radial direction of the clip projecting/retracting passage around the breakable portion when a pulling force over a predetermined value is applied to the clip and the clip operating part, and the clip apparatus further comprising:

an engaging portion excessive opening preventing structure which prevents the engaging portion from opening over the opening position while the distal end portion of the connecting member is directed outward in the radial direction of the clip projecting/retracting passage around the breakable portion by the deviating force;

wherein the engaging portion excessive opening preventing structure includes an opening restriction portion which projects from the rear end of the engaging portion and which has an abutting region configured to abut a part of an inner periphery of the passage near the opening of the passage at the distal end portion of the insertion part while the engaging portion opens at the open position; and the breakable portion of the connecting member is configured by cutting a part of an outer periphery of the connecting member between the distal end portion and the proximal end portion in a diametrical direction of the clip holding member to cross an extending direction of the clip projecting/retracting passage.

2. The clip apparatus according to claim 1, wherein the abutting region of the opening restriction portion, which abuts the part of the inner periphery of the passage near the opening of the passage at the distal end portion of the insertion part, is configured by a slope inclined inward in a radial direction of the passage of the insertion part as separating from the opening of the passage at the distal end portion of the insertion part along an extending direction of the passage.

3. A clip apparatus for ligaturing a living tissue, comprising:

an insertion part which can be inserted into a forceps channel of an endoscope inserted into a body cavity of a living tissue, and which includes a longitudinally extending passage extending along a longitudinal direction thereof;

a clip unit which includes a clip having slender arms capable of elastically opening and closing distal end portions thereof around mutually connected proximal ends thereof, and which can be projected from and retracted into the passage of the insertion part through an opening at a distal end portion of the insertion part; and a clip operating part which extends in the passage of the insertion part, which includes an external operation portion exposed at a proximal end portion of the insertion part and a clip connecting portion connected to the clip unit, and which operates the projection and retraction of the clip by the external operation portion;

the clip unit including:

a clip holding member which is housed in the passage of the insertion part to project from and to be retracted into the passage through the opening at the distal end portion, and which has a clip projecting/retracting passage in which the clip is housed to project from and to be retracted into the clip projecting/retracting passage so that the slender arms of the clip open and close the distal end portions thereof elastically;

an engaging portion, which is cut out from a circumferential wall of the clip holding member to be connected only at its one end to the circumferential wall of the clip holding member, which can open and close elastically around the one end thereof in a radial direction of the clip projecting/retracting passage between an open position and a closed position, and which opens and closes elastically by the projection and retraction of the clip holding member from and into the passage of the insertion part, a rear end of the engaging portion engaging with an end of the distal end portion of the insertion part to prevent the retraction of the clip holding member into the passage through the opening at the distal end portion of the insertion part while the engaging portion opens at the open position, and a connecting member which is movably housed in the clip projecting/retracting passage of the clip holding member, which has a distal end portion, a proximal end portion, and a breakable portion between the distal end portion and the proximal end portion, the distal end portion being connected to the proximal ends of the clip, the proximal end portion being connected to the clip connecting portion of the clip operating part, and the breakable portion being off to and in parallel with a longitudinal center line of the clip projecting/retracting passage in the radial direction of the clip projecting/retracting passage, and in which a deviating force is generated in the distal end portion to direct the distal end portion outward in the radial direction of the clip projecting/retracting passage around the breakable portion when a pulling force over a predetermined value is applied to the clip and the clip operating part, and the clip apparatus further comprising:

an engaging portion excessive opening preventing structure which prevents the engaging portion from opening over the opening position while the distal end portion of the connecting member is directed outward in the radial direction of the clip projecting/retracting passage around the breakable portion by the deviating force;

wherein the engaging portion excessive opening preventing structure includes a setting of a distance from the opening of the clip projecting/retracting passage at the distal end of the clip holding member to the one end of the engaging portion, longer than a distance from the distal ends of the arms of the clip to a distal end of the distal end portion of the connecting member; and the breakable portion of the connecting member is configured by cutting a part of an outer periphery of the connecting member between the distal end portion and the proximal end portion in a diametrical direction of the clip holding member to cross an extending direction of the clip projecting/retracting passage.

4. A clip apparatus for ligaturing a living tissue, comprising:

an insertion part which can be inserted into a forceps channel of an endoscope inserted into a body cavity of a living tissue, and which includes a longitudinally extending passage extending along a longitudinal direction thereof;

a clip unit which includes a clip having slender arms capable of elastically opening and closing distal end portions thereof around mutually connected proximal ends thereof, and which can be projected from and retracted into the passage of the insertion part through an opening at a distal end portion of the insertion part; and a clip operating part which extends in the passage of the insertion part, which includes an external operation portion exposed at a proximal end portion of the insertion part and a clip connecting portion connected to the clip unit, and which operates the projection and retraction of the clip by the external operation portion;

the clip unit including:

a clip holding member which is housed in the passage of the insertion part to project from and to be retracted into the passage through the opening at the distal end portion, and which has a clip projecting/retracting passage in which the clip is housed to project from and to be retracted into the clip projecting/retracting passage so that the slender arms of the clip open and close the distal end portions thereof elastically;

an engaging portion, which is cut out from a circumferential wall of the clip holding member to be connected only at its one end to the circumferential wall of the clip holding member, which can open and close elastically around the one end thereof in a radial direction of the clip projecting/retracting passage between an open position and a closed position, and which opens and closes elastically by the projection and retraction of the clip holding member from and into the passage of the insertion part, a rear end of the engaging portion engaging with an end of the distal end portion of the insertion part to prevent the retraction of the clip holding member into the passage through the opening at the distal end portion of the insertion part while the engaging portion opens at the open position, and a connecting member which is movably housed in the clip projecting/retracting passage of the clip holding member, which has a distal end portion, a proximal end portion, and a breakable portion between the distal end portion and the proximal end portion, the distal end portion being connected to the proximal ends of the clip, the proximal end portion being connected to the clip connecting portion of the clip operating part, and the breakable portion being off to and in parallel with a longitudinal center line of the clip projecting/retracting passage in the radial direction of the clip projecting/retracting passage, and in which a deviating force is generated in the distal end portion to direct the distal end portion outward in the radial direction of the clip projecting/retracting passage around the breakable portion when a pulling force over a predetermined value is applied to the clip and the clip operating part, and the clip apparatus further comprising:

an engaging portion excessive opening preventing structure which prevents the engaging portion from opening over the opening position while the distal end portion of the connecting member is directed outward in the radial direction of the clip projecting/retracting passage around the breakable portion by the deviating force;

wherein the engaging portion excessive opening preventing structure includes separating a position of the inner periphery of the clip projecting/retracting passage of the clip holding member to which the deviating force is applied by the distal end portion of the connecting member, from the engaging portion in the circumferential wall of the clip holding member in a circumferential direction of the clip projecting/retracting passage over more than 45 degrees; and the breakable portion of the connecting member is configured by cutting a part of an outer periphery of the connecting member between the distal end portion and the proximal end portion in a diametrical direction of the clip holding member to cross an extending direction of the clip projecting/retracting passage.

* * * * *